United States Patent
Machida et al.

(10) Patent No.: US 6,268,528 B1
(45) Date of Patent: Jul. 31, 2001

(54) METHOD OF PRODUCING NAPHTHALENEDICARBOXYLIC ACID

(75) Inventors: Hiroshi Machida; Fumiya Zaima; Masato Inari; Hiroshi Watanabe; Emiko Yokose, all of Okayama-ken (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 09/432,783

(22) Filed: Nov. 3, 1999

(30) Foreign Application Priority Data

Apr. 11, 1998 (JP) .................................................. 10-313077
Nov. 6, 1999 (JP) .................................................. 11-165383

(51) Int. Cl.$^7$ .................................................... C07C 51/16
(52) U.S. Cl. .............................................................. 562/412
(58) Field of Search ................................................ 562/412

(56) References Cited

U.S. PATENT DOCUMENTS 5,183,933  2/1993  Harper et al. .

FOREIGN PATENT DOCUMENTS

| 2310210 | 8/1997 | (GB) . |
| 51-97592 | 8/1976 | (JP) . |
| 53-104590 | 9/1978 | (JP) . |
| 56-3337 | 1/1981 | (JP) . |
| 60-89445 | 5/1985 | (JP) . |
| 1-121237 | 5/1989 | (JP) . |
| 6-65143 | 3/1994 | (JP) . |
| 7-48314 | 2/1995 | (JP) . |
| 8-143511 | 6/1996 | (JP) . |
| 8-193049 | 7/1996 | (JP) . |
| WO98/42649 | 10/1998 | (WO) . |

*Primary Examiner*—Paul J. Killos
(74) *Attorney, Agent, or Firm*—Antonelli, Terry, Stout & Kraus, LLP

(57) ABSTRACT

Dialkylnaphthalene is oxidized to naphthalenedicarboxylic acid in a lower aliphatic carboxylic acid solvent in the presence of a catalyst comprising a cobalt compound, a manganese compound and a bromine compound having an atomic ratio of manganese to cobalt of 0.03 to 0.5. The catalyst is supplied to the oxidation reaction zone so that the total amount of cobalt and manganese is 0.025 to 0.1 gram atom based on 1 gram mol of the dialkylnaphthalene. An oxidation product slurry is subjected to solid-liquid separation when the concentration of the naphthalenedicarboxylic acid in the slurry is 8 to 30% by weight. The process prevents the by-production of benzotricarboxylic acid such as trimellitic acid, thereby drastically reducing the incorporation of heavy metal complexes with trimellitic acid into naphthalenedicarboxylic acid crystals. The process optionally includes the addition of a polymer flocculant, this forming crystal aggregates with a large particle size and facilitating the separation of the crystals from the mother liquor.

23 Claims, No Drawings

METHOD OF PRODUCING NAPHTHALENEDICARBOXYLIC ACID

FIELD OF THE INVENTION

The present invention relates to a method of producing a naphthalenedicarboxyihc acid by a liquid phase oxidation of a dialkylnaphthalene, and a method of easily separating and recovering naphthalenedicarboxylic acid crystals formed by the liquid phase oxidation.

BACKGROUND OF THE INVENTION

The naphthalenedicarboxylic acid and its ester, particularly 2,6-naphthalenedicarboxylic acid (hereinafter referred to as "2,6-NDCA") and its ester are useful compounds for preparing high performance polyesters. Conventionally, 2,6-NDCA has been prepared by oxidizing 2,6-dialkylnaphthalene, 2,6-diacylnaphthalene or their derivatives in a solvent containing a lower aliphatic carboxylic acid in the presence of a catalyst containing cobalt, manganese and bromine. Such a process is disclosed in Japanese Patent Publication No. 56-3337, Japanese Patent Application Laid-Open No. 60-89445, U.S. Pat. No. 5,183,933, etc.

Unlike the preparation of terephthalic acid by the oxidation of p-xylene, the oxidation of the dialkylnaphthalene is generally accompanied by a remarkable by-production of benzotricarboxylic acid, particularly trimellitic acid (hereinafter referred to as "TMA") is by-produced from 2,6-naphthalenedicarboxylic acid due to the cleavage of the naphthalene ring. In addition, the by-produced benzotricarboxylic acid such as TMA, etc. forms, together with cobalt, manganese, etc. in the heavy metal catalyst, a complex sparingly soluble in the solvent comprising a lower aliphatic carboxylic acid, thereby deactivating the heavy metal catalyst. The decreased amount of the effective heavy metal catalyst due to the deactivation further increases the by-production of TMA, this in turn promoting the deactivation of the heavy metal catalyst. With such a vicious circle, the oxidation reaction is ceased in the worst case.

To avoid the deactivation of the heavy metal catalyst due to the accumulation of the by-produced TMA by recycling the mother liquor, proposed is a method of increasing the concentration of the heavy metal catalyst such as cobalt, manganese, etc. so as to compensate for the decrease of the effective amount due to the formation of the TMA-heavy metal complexes (U.S. Pat. No. 5,183,933, Japanese Patent Application Laid-Open No. 7-48314, etc.). In particular, U.S. Pat. No. 5,183,933 teaches that it is advantageous to use as much manganese as possible because manganese is less expensive than cobalt. However, the use of a greater amount of the heavy metals contaminates 2,6-NDCA crystals with a large amount of the TMA-heavy metal complexes to increase the content of the heavy metals in the crystals. The incorporation of the heavy metals into the crystals is a loss of the catalyst, and causes clogging of conduits in the purification process of 2,6-NDCA.

Several methods have been proposed to remove the incorporated TMA-heavy metal complexes in 2,6-NDCA crystals and recover the heavy metal catalyst. For example, Japanese Patent application Laid-Open No. 1-121237 discloses a method utilizing the relatively high water solubility of the TMA-heavy metal complexes, where 2,6-NDCA crystals are washed with water and the heavy metals in the washings are recovered in the insoluble carbonate forms by adding to the washings a compound forming carbonate ions. U.S. Pat. No. 5,183,933 teaches to add water to the oxidation reaction mixture to increase the water content in the low molecular weight carboxylic acid solvent, thereby dissolving the TMA-heavy metal complexes. Then, 2,6-NDCA crystals are separated from the solvent by a solid-liquid separation.

However, the method of Japanese Patent Application Laid-Open No. 1-121237, where the heavy metals incorporated in 2,6-NDCA are recovered by washing with water, is not practical for industrial scale process because the waste water after recovering the heavy metals requires expensive treatment for removing organic compounds such as TMA dissolved therein. The method of U.S. Pat. No. 5,183,933 is energy-consuming because water must be removed from the mother liquor before the catalyst and the lower aliphatic carboxylic acid are recovered and reused.

In the known method of producing 2,6-NDCA by the oxidation of 2,6-dialkylnaphthalene, as mentioned above, an excessive amount of the heavy metal catalyst must be used because the heavy metal catalyst is deactivated by the by-produced TMA, this causing in turn a large amount incorporation of TMA-heavy metal complexes into 2,6-NDCA crystals. Further, since the recycling of the mother liquor accumulate TMA in the reaction zone, much more excessive amount of heavy metal catalyst is required to result in the incorporation of a significantly increased amount of TMA-heavy metal complexes into 2,6-NDCA crystals. Since the recovery of the heavy metal catalyst incorporated in 2,6-NDCA requires a great amount of water, the heavy metal catalyst components and the solvent (lower aliphatic carboxylic acid) cannot be efficiently recovered.

The known method of producing the naphthalenedicarboxylic acid has encountered another problem. Since the crystals of naphthalenedicarboxylic acid formed by the oxidation reaction has an extremely small particle size, a solid-liquid separation for separating the crystals and solvent such as a centrifugal sedimentation, a centrifugal filtration and a suction filtration usually employed in the industrial process involves problems of a slow sedimentation or a low filtration speed, causing an increased amount of crystals remaining in the mother liquor, a clogging of filter, etc.

To facilitate the separation, several methods where the oxidation reaction was conducted under specific conditions for forming naphthalenedicarboxylic acid crystals having a larger particle size have been proposed. For example, a method of conducting the oxidation reaction at a specific temperature range of 180 to 220° C. (Japanese Patent Application Laid-Open No. 6-65143), a method of conducting the oxidation reaction under a low oxygen concentration (Japanese Patent Application Laid-Open No. 8-143511), and a method of adding an ester mixture containing dimethyl naphthalenedicarboxylate (Japanese Patent Application Laid-Open No. 8-193049) have been known.

In the above methods of conducting the oxidation reaction under specific conditions to form naphthalenedicarboxylic acid crystals having a larger particle size, the particle size achieved is, at most, about 40 $\mu$m and the improvement in facilitating the solid-liquid separation by increasing sedimentation and filtration speed and avoiding the crystals from remaining in the mother liquor is insufficient.

Thus, an object of the present invention is to provide a method of producing naphthalenedicarboxylic acid by oxidation reaction of dialkylnaphthalene suitable for industrial-scale process and that can efficiently recover the heavy metal catalyst and solvent.

Another object of the present invention is to provide an industrially advantageous method of producing naphthalenedicarboxylic acid by oxidation reaction of dialkylnaphthalene to form naphthalenedicarboxylic acid crystals having a larger particle size capable of facilitating the separation and recovery of the crystals.

SUMMARY OF THE INVENTION

The inventors have made extensive studies on the reaction conditions to solve the above problems involved in the conventional method of producing naphthalenedicarboxylic acid by the oxidation of dialkylnaphthalene. As a result thereof, the oxidation under specific conditions in the presence of a catalyst with a low manganese content and a relatively increased cobalt content and the subsequent crystallization of the naphthalenedicarboxylic acid carried out at a specific concentration range of the naphthalenedicarboxylic acid in an oxidation product mixture provide the naphthalenedicarboxylic acid in a high yield as well as prevent the benzotricarboxylic acid-heavy metal complexes from incorporating into the naphthalenedicarboxylic acid crystals to extremely reduce the heavy metal content in the crystals, thereby facilitating the efficient recovery of the heavy metal catalyst and the solvent.

Further, as a result of extensive study on forming naphthalenedicarboxylic acid crystals having a larger particle size, the inventors have found that the addition of a polymer flocculant to an oxidation product mixture aggregates the naphthalenedicarboxylic acid crystals to form crystals having a large particle size, thereby drastically facilitating the solid-liquid separation of the crystals from the mother liquor. The present invention has been accomplished based on these findings.

Thus, in a first aspect of the present invention, there is provided a method of producing naphthalenedicarboxylic acid, which comprises the steps of (1) oxidizing dialkylnaphthalene to naphthalenedicarboxylic acid at 160 to 240° C. in a solvent containing a lower aliphatic carboxylic acid using a molecular oxygen-containing gas in the presence of a catalyst comprising a cobalt compound, a manganese compound and an bromine compound to obtain a oxidation product mixture, and (2) subjecting the oxidation product mixture to a solid-liquid separation to obtain crystals of naphthalenedicarboxylic acid and a mother liquor when a concentration of naphthalenedicarboxylic acid in the oxidation product mixture is 8 to 30% by weight, an atomic ratio of manganese to cobalt of the catalyst being 0.03 to 0.5, and the catalyst being supplied to an oxidation reaction zone so that a total of cobalt and manganese is 0.025 to 0.1 gram atom based on 1 gram atom of the dialkylnaphthalene.

In a second aspect of the present invention, there is provided a method of producing naphthalenedicarboxylic acid wherein a polymer flocculant is added, in the above method, to the oxidation reaction zone or the oxidation product mixture prior to the solid-liquid separation.

DETAILED DESCRIPTION OF THE INVENTION

The starting dialkylnaphthalene used in the method of the present invention may include dimethylnaphthalenes, diethylnaphthalenes, diisopropylnaphthalenes and their functionally oxidized derivatives. The 2,6-isomers of the dialkylnaphthalene are generally used for preparing the materials for high performance polyesters, and due primary to availability, 2,6-dimethylnaphthalene is preferably used.

The lower aliphatic carboxylic acid used as the solvent for the liquid phase oxidation may include formic acid, acetic acid, propionic acid, butyric acid and a mixture thereof. In view of its heat stability and non-corrosive nature, acetic acid is most preferable. The solvent may contain water in an amount of preferably 30% by weight or less, more preferably 20% by weight or less, and particularly preferably 15% by weight or less. An excessive amount of water is likely to increase the by-production of the benzotricarboxylic acid such as TMA. The solvent is used 1 to 20 times, preferably 2 to 15 times the weight of the starting dialkylnaphthalene.

The oxidation catalyst used in the present invention comprises a cobalt compound, a manganese compound and a bromine compound. The oxidation catalyst may optionally contain, if desired, a compound of another heavy metal such as iron, cerium and nickel. The compound of cobalt, manganese and other heavy metals may be a salt of organic acid, a hydroxide, a halide, a carbonate, etc., and preferably an acetate and a bromide. Any bromine compound may be used as far as it dissolves in the reaction system and generates bromide ions therein, and exemplified by an inorganic bromide such as hydrogen bromide, sodium bromide, cobalt bromide and manganese bromide, and a brominated organic compound such as bromoacetic acid. Preferred are hydrogen bromide, cobalt bromide and manganese bromide.

The conditions for the oxidation reaction are selected so as to prevent the complexes between the by-produced TMA, etc. and the heavy metal catalyst components from incorporating into the crystals of 2,6-NDCA, etc. From the inventors' study, the solubility of the TMA-heavy metal complexes has been proved to be represented by the solubility product as is the case of the solubility of usual electrolytes. Therefore, the reaction conditions capable of making the product between the concentration of the by-produced TMA, etc. and the concentration of the heavy metal catalyst more smaller are preferred to prevent the TMA-heavy metal complexes from incorporating into the crystals of 2,6-NDCA, etc. In addition, the inventors have found that the TMA-manganese complex is less soluble than the TMA-cobalt complex in the lower aliphatic carboxylic acid solvent and easily incorporates into 2,6-NDCA crystals. Consequently, the inventors have determined that the incorporation of the TMA-heavy metal complexes into 2,6-NDCA can be significantly minimized by reducing the amount of manganese to the minimum limit being required and relatively increasing the amount of cobalt.

In view of the foregoing, the amounts of the catalyst used in the oxidation reaction is determined so that manganese, cobalt and other optional metals are introduced into a reactor in the respective amount ranges specified below.

Cobalt and manganese are supplied to a reactor so that the amount of cobalt and manganese in total is 0.025 to 0.1 gram atom, preferably 0.03 to 0.08 gram atom based on 1 gram mol of the starting dialkylnaphthalene. Within the above range, the higher the amount of the catalyst metals used, the lower the amount of the by-produced TMA, thereby ensuring the production of 2,6-NDCA in a higher yield. The use of cobalt and manganese in an amount exceeding the above range produces no further improvement, and detrimentally causes a large amount incorporation of the complexes of an excessive catalyst metals with TMA into 2,6-NDCA crystals. When the amount of the heavy metal catalyst used is smaller than the above range, the by-production of TMA is increased to result in a large amount incorporation of the TMA-heavy metal complexes into the crystals, which may cease the oxidation reaction in the worst case.

The atomic ratio of manganese to cobalt in the heavy metal catalyst is 0.03 to 0.5, preferably 0.05 to 0.4, and more preferably 0.07 to 0.3. A ratio exceeding the above range causes a large amount incorporation of TMA-heavy metal complexes into the crystals. When the ratio is smaller than the above range, the by-production of TMA increases to also cause a large amount incorporation of TMA-heavy metal complexes into the crystals.

Bromine is supplied to the reactor so that the total amount is 0.005 to 0.3 gram atom, preferably 0.01 to 0.15 gram atom, and more preferably 0.02 to 0.1 gram atom based on 1 gram mol of the dialkylnaphthalene. Within the above range, the larger the amount of bromine used, the by-production of TMA is reduced and the solubility of the TMA-heavy metal complexes in the mother liquor is increased. The use of bromine exceeding the above range unfavorably increases the bromination on the naphthalene ring and the production of colored products. When the amount of bromine used is smaller than the above range, the by-production of TMA increases to increase the incorporation amount of the TMA-heavy metal complexes into the crystals.

The oxidation temperature is 160 to 240° C., and preferably 180 to 220° C. A reaction temperature lower than the above range unfavorably produces a large amount of TMA and reaction intermediates such as 6-formyl-2-naphtoic acid. A reaction temperature higher than the above range is undesirable because no additional effect on reducing the by-production of TMA is obtained and an increased amount of the lower aliphatic carboxylic acid solvent is lost by combustion.

The oxidation pressure is 5 to 40 kgf/cm$^2$ G, preferably 10 to 30 kgf/cm$^2$ G. The oxygen partial pressure in the reactor is preferably 0.005 kgf/cm$^2$ (absolute pressure) or higher. When the oxygen partial pressure is less than the above range, an extreme amount of the reaction intermediates is produced to lower the yield of 2,6-NDCA.

A source of the molecular oxygen-containing gas may include oxygen gas, a mixed gas of oxygen and an inert gas such as nitrogen and argon, and air is most usually used.

The oxidation reaction may be conducted in any of a batch manner, semi-batch manner or continuous manner, and the semi-batch or continuous manner is preferable.

Crystals of the naphthalenedicarboxylic acid formed by the oxidation reaction are separated from the solvent, i.e., the mother liquor by solid-liquid separation (first solid-liquid separation). In the process of the present invention, the solid-liquid separation is conducted when the naphthalenedicarboxylic acid concentration in the oxidation product slurry or mixture is 8 to 30% by weight, preferably 10 to 25% by weight, and more preferably 12 to 20% by weight. When the naphthalenedicarboxylic acid concentration in the oxidation product slurry is higher than the above range, a large amount of TMA, etc. is by-produced to result in a large amount incorporation of the TMA-heavy metal complexes into the separated naphthalenedicarboxylic acid crystals. By using a larger amount of the solvent, the concentration of the naphthalenedicarboxylic acid as well as the concentrations of TMA and the heavy metal catalyst can be reduced to ensure the inhibition of forming the TMA-heavy metal complexes. However, since the load required for the solid-liquid separator becomes extremely large, the use of an excessively large amount of solvent is not desirable.

If the concentration of the naphthalenedicarboxylic acid in the oxidation product slurry effluent form the oxidation reactor is higher than the above range, the concentration may be adjusted to fall within the above range by diluting the slurry with the lower aliphatic carboxylic acid. If lower than the above range, the concentration may be adjusted to fall within the above range by condensing the slurry by the evaporating the solvent under heating.

If desired, a compound capable of forming bromide ions may be added to the oxidation product slurry to increase the solubility of the TMA-heavy metal complexes, thereby dissolving the TMA-heavy metal complexes incorporated into the crystals. Then, the crystals are separated by the solid-liquid separation to obtain the crystals having a reduced amount of the incorporated TMA-heavy metal complexes. The compound capable of forming bromide ions may be hydrobromic acid, sodium bromide, potassium bromide, etc., and hydrobromic acid is particularly preferable. The compound capable of forming bromide ions is added so that the concentration of bromide ions in the oxidation product slurry is preferably 2000 to 6000 ppm, more preferably 3000 to 5000 ppm.

In the present invention, it is preferable to use a polymer flocculant to facilitate the first solid-liquid separation by forming aggregates of the naphthalenedicarboxylic acid crystals.

Although some polymer flocculant may be directly added to the oxidation reactor, the polymer flocculant is preferably added to the oxidation product slurry or mixture containing the naphthalenedicarboxylic acid crystals from the oxidation reactor.

The polymer flocculant is a water-soluble polymer usually used for flocculating suspended solid particles in tap or waste water. The polymer flocculant is adsorbed on the suspended solid particles to crosslink the solid particles to each other, thereby flocculating them. In the present invention, known anionic, nonionic, cationic or amphoteric polymer flocculants may be used. For example, the anionic polymer flocculant includes sodium polyacrylate and acrylic amide-sodium acrylate copolymer; the nonionic polymer flocculant includes polyacrylic amide, starch and gelatin; the cationic polymer flocculant includes Mannich-modified polyacrylic amide, polyalkylaminoacrylate, polyakylaminomethacrylate and chitosan; and the amphoteric polymer Ilocculant includes acrylic amide-aminoalkylacrylate quaternary salt-acrylic acid copolymer. These polymer flocculants may be used alone or in combination of two or more. An inorganic flocculant such as aluminum sulfate and polychloroaluminum may be combinedly used.

The polymer flocculant is in the form of powder and liquid. The powdery polymer flocculant may be used directly or as a solution in water or water-containing acetic acid. The liquid polymer flocculant may be used without diluting or after diluted with water or water-containing acetic acid.

The addition amount of the polymer flocculant is preferably 0.005 to 0.4% by weight, more preferably 0.005 to 0.3% by weight, and particularly preferably 0.01 to 0.15% by weight based on the amount of the naphthalenedicarboxylic acid crystals. When less than 0.005% by weight, no remarkable flocculating effect is obtained. An addition amount exceeding 0.4% by weight produces no additional effect and deteriorates the efficiency of filter due to the adhesion of excess flocculant to the filter.

The mixing of the flocculant with the oxidation product slurry may be effected by a reactor equipped with a rotary stirrer or an agitating pump, a continuous mixer such as a ribbon blender and a paddle agitator, and an in-line blender such as a line mixer and a static mixer.

The oxidation product slurry optionally added with the polymer flocculant is separated into the crystals and the solvent, i.e., the mother liquor by the solid-liquid separation using a solid-liquid separator such as a centrifugal decanter, a centrifugal filter and a vacuum falter. The minimum particle size to be effectively separated is about 5 μm or larger for the centrifugal decanter and 10 to 20 μm for the centrifugal filter and vacuum filter. Since the particle size of the naphthalenedicarboxylic acid crystals achieved in the conventional process is extremely small, the centrifugal decanter has been mainly used. Since the particle size of the naphthalenedicarboxylic acid crystals becomes as large as 60 to 150 μm by the use of the polymer flocculant, the preferred embodiment of the present invention makes it possible to efficiently use the centrifugal filter and vacuum filter which are rather difficult to be applied to the conventional process, and additionally, increases the throughput of the centrifugal decanter. Thus, the solid-liquid separation in the process of the present invention is conducted economically and advantageously.

Since the cake (crystals) obtained by solid-liquid separating the oxidation product using the separator contains the mother liquor dissolving impurities and the oxidation catalyst, the cake is preferably washed to obtain the naphthalenedicarboxylic acid crystals with a higher purity. The washing of the crystals may be made by (1) a method where the mother liquor in the crystals is replaced with a washing liquid by contacting the crystals with the washing liquid in the separator, and (2) a method where the crystals (cake) obtained by solid-liquid separating the oxidation product is redispersed in a solvent containing a lower aliphatic carboxylic acid and then the resulting dispersion is solid-liquid separated again (second solid-liquid separation).

At least a portion of the mother liquor from the second solid-liquid separation may be recycled to the oxidation product slurry of the next run, and then the resultant oxidation product slurry is subjected to the first solid-liquid separation. With such a recycling, the amount of the lower aliphatic carboxylic acid used in the washing process can be reduced.

Water and the lower aliphatic carboxylic acid are preferably used as the washing liquid. In the process of the present invention, there is no need to dissolve the TMA-heavy metal complexes in an extreme amount of water, and a lower aliphatic carboxylic acid having a water content of 10% or less is sufficient for the washing. The amount of the washing liquid used is preferably 0.5 to 4 times the weight of the cake, i.e., crystals.

The conventional process requires an extreme amount of water to reduce the catalyst heavy metal components incorporated into the crude crystals of naphthalenedicarboxylic acid, this making it difficult to recover the catalyst component from the washings. In the process of the present invention, since the washing is effected with a lower aliphatic carboxylic acid having a water content of 10% or less, the washings can be reused in the next oxidation reaction without any additional pretreatment, thereby significantly reducing the amount of water accumulated in the system. Thus, according to the present invention, the catalyst components and the solvent can be effectively recovered and reused in the subsequent oxidation reaction without consuming a large quantity of energy.

The crude crystals of naphthalenedicarboxylic acid obtained through the liquid-solid separation and the subsequent washing are made into the materials for producing high performance polyesters by purification or esterification with methanol to dimethyl naphthalenedicarboxylate followed by purification. In the conventionally known process, large heavy metal catalyst components in the crude naphthalenedicarboxylic acid crystals cause the problems such as clogging of conduits in the purification process. In the present invention, the process is free from such problems because the heavy metal contents of the crude naphthalenedicarboxylic acid crystals are as small as about 0.01 to 0.06% by weight for cobalt and about 0.003 to 0.05% by weight for manganese.

The mother liquor from the solid-liquid separation contains the most part of the oxidation catalyst components. Since the catalyst components, particularly the heavy metal components are expensive, the catalyst components are preferably recovered from the mother liquor for reusing. A convenient method for reusing the catalyst usually employed is to recycle the mother liquor to the reactor without any pretreatments. However, in the process of the present invention, since the most part of the by-produced TMA, etc. is contained in the mother liquor, the recycling of the mother liquor into the reactor accumulates TMA, etc. in the oxidation reaction zone to cause the incorporation of the TMA-heavy metal complexes into the crystals. Therefore, it is not preferable to recycle a substantial part of the mother liquor into the reactor, and the amount of the mother liquor to be recycled into the reactor should be determined so as to avoid the formation of the TMA-heavy metal complexes in the oxidation reaction zone.

In the present invention, the catalyst in the mother liquor is preferably reused after the catalyst components are chemically or physically recovered from the mother liquor. Known methods may be used to recover the catalyst components. For example, Japanese Patent Application Laid-Open No. 51-97592 discloses to form oxalic acid salt of the catalyst metals by adding oxalate ions to the mother liquor and collect the salt thus formed, and Japanese Patent Application Laid-Open No. 53-104590 discloses to recover the catalyst components by ion exchange resin.

Of the known methods for recovering the catalyst components, the recovery by anion exchange resin is particularly preferable because not only the heavy metal components but also bromide ions are simultaneously recovered. Any of strongly or weakly basic anion exchange resins having primary, secondary or tertiary amino groups and quaternary ammonium groups may be used. Specifically, Amberlite IRA-900, Amberlite IRA-96SB (trademarks of Oregano Co., Ltd.), Dowex I-X4 (trademark of The Dow Chemical Company), Diaion SA10 (trademark of Mitsubishi Chemical Corporation), etc. may be exemplified. The water content of the mother liquor being treated by the anion exchange resin is preferably 15% by weight. A water content exceeding 15% by weight results in an insufficient recovery of the metals. Since, in the present invention, the water contents of the mother liquor and the washings for the crude naphthalenedicarboxylic acid crystals are in the levels lower than 15% by weight, the mother liquor and the washings are directly subjected to catalyst recovering treatment by anion exchange resins without needing any additional treatment, such as distillation, for reducing the water content.

The anion exchange resin adsorbs bromide ions simultaneously in an amount 2 times the total molar amount of cobalt and manganese as the catalyst components. Therefore, the molar ratio of bromide ions to the metal components in the mother liquor to be subjected to anion exchange treatment is preferably 2 or more. If necessary, a compound capable of forming bromide ions, such as hydrobromic acid, may be added to the mother liquor to ensure the above molar ratio range. The metals and bromine adsorbed on the anion exchange resin are eluted with water or a lower aliphatic carboxylic acid having a water content of 15% by weight, preferably 25% by weight.

By the method of using the anion exchange resin or oxalic acid, as evident from the examples mentioned below, the recovery of the heavy metal, particularly expensive cobalt, reaches 99% or more, thereby reducing the loss of cobalt with the mother liquor to an extremely small level.

The present invention will be described in further detail by way of the following Examples which are not to be construed as limiting the invention.

In Table 1, DMN, Co+Mn represent the supplied amount of the starting 2,6-dimethylnaphthalene, and the supplied amount of cobalt catalyst and manganese catalyst in total, respectively. In Tables 1 to 3, the cobalt residue is a ratio of the residual amount of cobalt in the crystals to the supplied amount of cobalt. The same is applied to the manganese residue.

EXAMPLE 1

Cobalt acetate tetrahydrate, manganese acetate tetrahydrate, 47% by weight hydrobromic acid and water were dissolved into glacial acetic acid to prepare 320 g catalyst solution having a cobalt content of 0.20% by weight, a manganese content of 0.05% by weight, a bromine content of 0.30% by weight and a water content of 3% by weight.

Into a 500 ml titanium autoclave equipped with a stirrer, a reflux condenser and a feed pump for supplying a starting solution, were charged 120 g of the catalyst solution. Separately, a mixture of the remaining 200 g catalyst solution and 40 g 2,6-dimethylnaphthalene was charged into a feed tank and heated therein to dissolve 2,6-dimethylnaphthalene, thereby preparing the starting solution.

The inner pressure of the autoclave was adjusted to 18 kgf/cm$^2$ G by introducing nitrogen gas and the contents was heated to 200° C. under stirring. After the temperature and pressure reached steady states, the oxidation reaction was permitted to proceed by supplying the starting solution and compressed air to the reactor. The starting solution was continuously supplied to the reactor over one hour while adjusting the flow rate of air so as to achieve about 2 volume % oxygen in the vent gas stream. After the starting solution was supplied entirely, the supply of air was continued until achieving about 10 volume % oxygen in the vent gas stream.

After completing the reaction, the autoclave was cooled to about 70° C. to take out the oxidation product which was then suction-filtered using a glass filter to obtain a cake and a mother liquor. The cake on the filter was washed with 80 g glacial acetic acid and dried to obtain 52.6 g crude 2,6-NDCA crystals. The composition of the crystals thus obtained and the yields are shown in Table 1a. The heavy metal contents in the crystals were very small and 98.7% by weight of cobalt added and 97.9% by weight of manganese added were remained in the mother liquor.

EXAMPLE 2

The oxidation reaction was conducted in the same manner as in Example 1 except for using a starting solution having a cobalt content of 0.15% by weight, a manganese content of 0.06% by weight, a bromine content of 0.30% by weight and a water content of 3% by weight, to obtain 52.4 g crude 2,6-NDCA crystals.

The composition of the crystals thus obtained, the yields and the residue of the heavy metals in the crystals are shown in Table 1a.

EXAMPLE 3

The oxidation reaction was conducted in the same manner as in Example 1 except for using a starting solution having a cobalt content of 0.30% by weight, a manganese content of 0.05% by weight, a bromine content of 0.30% by weight and a water content of 3% by weight, to obtain 52.9 g crude 2,6-NDCA crystals.

The composition of the crystals thus obtained, the yields and the residue of the heavy metals in the crystals are shown in Table 1a.

EXAMPLE 4

The oxidation reaction was conducted in the same manner as in Example 1 except for changing the reaction temperature to 220° C. and the reaction pressure to 20 kgf/cm$^2$ G, to obtain 52.3 g crude 2,6-NDCA crystals.

The composition of the crystals thus obtained, the yields and the residue of the heavy metals in the crystals are shown in Table 1a.

EXAMPLE 5

The oxidation reaction was conducted in the same manner as in Example 1 except for changing the reaction temperature to 180° C. and the reaction pressure to 16 kgf/cm$^2$ G, to obtain 52.1 g crude 2,6-NDCA crystals.

The composition of the crystals thus obtained, the yields and the residue of the heavy metals in the crystals are shown in Table 1b.

EXAMPLE 6

Cobalt acetate tetrahydrate, manganese acetate tetrahydrate, 47% by weight hydrobromic acid and water were dissolved into glacial acetic acid to prepare 325 g catalyst solution having a cobalt content of 0.24% by weight, a manganese content of 0.04% by weight, a bromine content of 0.30% by weight and a water content of 3% by weight.

Into the same 500 ml titanium autoclave as used in Example 1, were charged 125 g of the catalyst solution. Separately, a mixture of the remaining 200 g catalyst solution and 50 g 2,6-dimethylnaphthalene was charged into a feed tank and heated therein to dissolve 2,6-dimethylnaphthalene, thereby preparing a starting solution. Then, the oxidation reaction was conducted in the same manner as in Example 1 to obtain 66.0 g crude 2,6-NDCA crystals.

The composition of the crystals thus obtained, the yields and the residue of the heavy metals in the crystals are shown in Table 1b.

COMPARATIVE EXAMPLE 1

The oxidation reaction was conducted in the same manner as in Example 1 except for using a starting solution having a cobalt content of 0.40% by weight, a manganese content of 0.10% by weight, a bromine content of 0.30% by weight and a water content of 3% by weight, to obtain 53.5 g crude 2,6-NDCA crystals.

The composition of the crystals thus obtained, the yields and the residue of the heavy metals in the crystals are shown in Table 1b. Although the by-production of TMA was decreased due to the use of increased amount of the heavy metal catalyst, the residue of the heavy metal catalyst, particularly manganese, in the crystals increased.

COMPARATIVE EXAMPLE 2

The oxidation reaction was conducted in the same manner as in Example 1 except for using a starting solution having a cobalt content of 0.08% by weight, a manganese content of 0.02% by weight, a bromine content of 0.30% by weight and a water content of 3% by weight, to obtain 50.7 g crude 2,6-NDCA crystals.

The composition of the crystals thus obtained, the yields and the residue of the heavy metals in the crystals are shown in Table 1b. The use of a small amount of the heavy metal catalyst reduced the yield of 2,6-NDCA and significantly increased the by-production of TMA and 2-formyl-6-naphthoic acid.

COMPARATIVE EXAMPLE 3

The oxidation reaction was conducted in the same manner as in Example 1 except for using a starting solution having a cobalt content of 0.15% by weight, a manganese content of 0.10% by weight, a bromine content of 0.30% by weight and a water content of 3% by weight, to obtain 52.9 g crude 2,6-NDCA crystals.

The composition of the crystals thus obtained, the yields and the residue of the heavy metals in the crystals are shown in Table 1c. Since the ratio of manganese to cobalt in the catalyst was high, a large amount of manganese remained in the 2,6-NDCA crystals and the residue of cobalt in the crystals was increased.

COMPARATIVE EXAMPLE 4

The oxidation reaction was conducted in the same manner as in Example 1 except for using a starting solution having a cobalt content of 0.25% by weight, a manganese content of 0.005% by weight, a bromine content of 0.30% by weight and a water content of 3% by weight, to obtain 51.0 g crude 2,6-NDCA crystals.

The composition of the crystals thus obtained, the yields and the residue of the heavy metals in the crystals are shown in Table 1c. Since the ratio of manganese to cobalt in the catalyst was extremely low, the yield of 2,6-NDCA was reduced and the residue of cobalt in the crystals was increased.

COMPARATIVE EXAMPLE 5

The oxidation reaction was conducted in the same manner as in Example 1 except for changing the reaction temperature to 150° C. and the reaction pressure to 14 kgf/cm$^2$ G, to obtain 50.8 g crude 2,6-NDCA crystals.

The composition of the crystals thus obtained, the yields and the residue of the heavy metals in the crystals are shown in Table 1c. A low reaction temperature resulted in a significant increase in by-production of TMA and 2-formyl-6-naphthoic acid and a low yield of 2,6-NDCA. Also, the residue of the heavy metal catalyst in the crystals was high.

TABLE 1a

|  | Examples | | | |
| --- | --- | --- | --- | --- |
|  | 1 | 2 | 3 | 4 |
| Reaction temperature (° C.) | 200 | 200 | 200 | 220 |
| Catalyst solution/DMN (weight ratio) | 8 | 8 | 8 | 8 |
| Composition of catalyst solution (wt. %) |  |  |  |  |
| Cobalt | 0.20 | 0.15 | 0.30 | 0.20 |
| Manganese | 0.05 | 0.06 | 0.05 | 0.05 |
| Bromine | 0.30 | 0.30 | 0.30 | 0.30 |
| (Co + Mn)/DMN (molar ratio) | 0.054 | 0.045 | 0.075 | 0.054 |
| Mn/Co (molar ratio) | 0.27 | 0.43 | 0.18 | 0.27 |
| 2,6-NDCA concentration in oxidation product (wt. %) | 13.5 | 13.4 | 13.6 | 13.5 |
| Water in mother liquor (wt. %) | 6.1 | 6.0 | 6.2 | 6.9 |
| Dried crystals (g) | 52.6 | 52.4 | 52.9 | 52.3 |
| Composition of dried crystals (wt. %) |  |  |  |  |
| 2,6-NDCA | 98.0 | 97.9 | 98.2 | 97.8 |
| TMA | 0.059 | 0.188 | 0.066 | 0.052 |
| 2-Formyl-6-naphthoic acid | 0.169 | 0.150 | 0.188 | 0.049 |
| Cobalt | 0.0160 | 0.0206 | 0.0246 | 0.0135 |
| Manganese | 0.0064 | 0.0285 | 0.0075 | 0.0058 |
| Yield (mol %) |  |  |  |  |
| 2,6-NDCA | 93.4 | 93.0 | 94.1 | 92.7 |
| TMA | 3.2 | 3.5 | 2.6 | 3.1 |
| 2-Formyl-6-naphthoic acid | 0.18 | 0.16 | 0.20 | 0.05 |
| Cobalt residue (%) | 1.3 | 2.3 | 1.4 | 1.1 |
| Manganese residue (%) | 2.1 | 7.8 | 2.5 | 1.9 |

TABLE 1b

|  | Examples | | Comparative Examples | |
| --- | --- | --- | --- | --- |
|  | 5 | 6 | 1 | 2 |
| Reaction temperature (° C.) | 180 | 200 | 200 | 200 |
| Catalyst solution/DMN (weight ratio) | 8 | 6.5 | 8 | 8 |
| Composition of catalyst solution (wt. %) |  |  |  |  |
| Cobalt | 0.20 | 0.24 | 0.40 | 0.08 |
| Manganese | 0.05 | 0.04 | 0.10 | 0.02 |
| Bromine | 0.30 | 0.30 | 0.30 | 0.30 |
| (Co + Mn)/DMN (molar ratio) | 0.054 | 0.049 | 0.108 | 0.022 |
| Mn/Co (molar ratio) | 0.27 | 0.18 | 0.27 | 0.27 |
| 2,6-NDCA concentration in oxidation product (wt. %) | 13.3 | 16.1 | 13.6 | 12.6 |
| Water in mother liquor (wt. %) | 5.9 | 6.8 | 6.2 | 6.0 |
| Dried crystals (g) | 52.1 | 66.0 | 53.5 | 50.7 |
| Composition of dried crystals (wt. %) |  |  |  |  |
| 2,6-NDCA | 97.5 | 98.2 | 97.4 | 94.7 |
| TMA | 0.171 | 0.063 | 0.582 | 0.071 |
| 2-Formyl-6-naphthoic acid | 0.529 | 0.199 | 0.205 | 1.67 |
| Cobalt | 0.0234 | 0.0228 | 0.0893 | 0.0064 |
| Manganese | 0.0226 | 0.0048 | 0.0842 | 0.0031 |
| Yield (mol %) |  |  |  |  |
| 2,6-NDCA | 92.0 | 93.9 | 94.3 | 87.1 |
| TMA | 3.7 | 2.8 | 2.2 | 5.8 |
| 2-Formyl-6-naphthoic acid | 0.55 | 0.21 | 0.22 | 1.7 |
| Cobalt residue (%) | 1.9 | 1.9 | 3.7 | 1.3 |
| Manganese residue (%) | 7.4 | 2.4 | 14.1 | 2.5 |

TABLE 1c

|  | Comparative Examples | | |
| --- | --- | --- | --- |
|  | 3 | 4 | 5 |
| Reaction temperature (° C.) | 200 | 220 | 150 |
| Catalyst solution/DMN (weight ratio) | 8 | 8 | 8 |
| Composition of catalyst solution (wt. %) | | | |
| Cobalt | 0.15 | 0.25 | 0.20 |
| Manganese | 0.10 | 0.005 | 0.05 |
| Bromine | 0.30 | 0.30 | 0.30 |
| (Co + Mn)/DMN (molar ratio) | 0.055 | 0.054 | 0.054 |
| Mn/Co (molar ratio) | 0.71 | 0.021 | 0.27 |
| 2,6-NDCA concentration in oxidation product (wt. %) | 13.4 | 13.0 | 12.4 |
| Water in mother liquor (wt. %) | 6.2 | 6.3 | 5.8 |
| Dried crystals (g) | 52.9 | 51.0 | 50.8 |
| Composition of dried crystals (wt. %) | | | |
| 2,6-NDCA | 97.0 | 97.7 | 93.0 |
| TMA | 0.714 | 0.206 | 1.31 |
| 2-Formyl-6-naphthoic acid | 0.217 | 0.245 | 2.43 |
| Cobalt | 0.0466 | 0.0503 | 0.161 |
| Manganese | 0.130 | 0.0038 | 0.150 |
| Yield (mol %) | | | |
| 2,6-NDCA | 92.9 | 90.3 | 85.7 |
| TMA | 3.2 | 4.9 | 6.3 |
| 2-Formyl-6-naphthoic acid | 0.23 | 0.25 | 2.5 |
| Cobalt residue (%) | 5.1 | 3.2 | 12.8 |
| Manganese residue (%) | 21.5 | 12.0 | 47.5 |

COMPARATIVE EXAMPLE 6

Cobalt acetate tetrahydrate, manganese acetate tetrahydrate, 47% by weight hydrobromic acid and water were dissolved into 7 kg glacial acetic acid to prepare a catalyst solution having a cobalt content of 0.60% by weight, a manganese content of 0.15% by weight, a bromine content of 0.75% by weight and a water content of 2% by weight.

Into a 5-liter titanium reactor equipped with a stirrer and a reflux condenser, were charged 1200 g of the catalyst solution. Separately, 2,6-dimethylnaphthalene with a purity of 99.7% by weight was melted in a tank by heating to 120° C. or higher.

The inner pressure of the reactor was adjusted to 14 kgf/cm$^2$ G by introducing nitrogen gas and the contents was heated to 200° C. under stirring. After the temperature and pressure reached steady states, the oxidation reaction was permitted to proceed while supplying the molten 2,6-dimethylnaphthalene at a flow rate of 300 g/hr and compressed air at a flow rate about 0.3 Nm$^3$/hr to the reactor. After 450 g 2,6-dimethylnaphthalene were supplied to the reactor (90 minutes after the initiation of oxidation reaction), the supply of the catalyst solution to the reactor was started at a flow rate of 800 g/hr while removing the oxidation product from the reactor to a receiving tank maintained at ordinary pressure so that the upper surface of the liquid in the reactor kept its level constant ((Co+Mn)/DMN=0.054 and Mn/Co=0.27).

After the reaction was continued for about 8 hours, the supply of 2,6-dimethylnaphthalene, the catalyst solution and air was stopped to cease the reaction, thereby obtaining 10.2 kg slurry of the oxidation product including the slurry remaining in the reactor. The concentration of 2,6-NDCA in the slurry was 30.8% by weight.

The yield based on 2,6-dimethylnaphthalene supplied was 94.8 mol % for 2,6-NDCA, 1.7 mol % for TMA and 0.27 mol % for 2-formyl-6-naphthoic acid.

A portion (1000 g) of the slurry was subjected to solid-liquid separation at about 70° C. by suction filtration using a glass filter. The cake on the filter was washed with 500 g glacial acetic acid and dried to obtain crude 2,6-NDCA crystals. The composition of the crystals thus obtained and the residue of the heavy metal catalyst in the crystals are shown in Table 2. Since the solid-liquid separation was conducted on the slurry having a high 2,6-NDCA concentration, an extremely large amount of the heavy metal catalyst remained in the crystals without being washed away by glacial acetic acid.

EXAMPLE 7

After adding 300 g acetic acid having a water content of 5% by weight to 1000 g oxidation product slurry obtained in Comparative Example 6, 47% by weight hydrobromic acid was further added so as to adjust the bromide ion concentration of the slurry to 5000 ppm. The resultant slurry was kept at about 70° C. for 15 minutes under stirring, and then, the slurry was subjected to solid-liquid separation by suction filtration using a glass filter. The cake on the filter was washed with 500 g glacial acetic acid and dried. The composition of the crude 2,6-NDCA crystals thus obtained and the residue of the heavy metal catalyst in the crystals are shown in Table 2.

EXAMPLE 8

After adding 800 g acetic acid having a water content of 5% by weight to 1000 g oxidation product slurry obtained in Comparative Example 6, 47% by weight hydrobromic acid was further added so as to adjust the bromide ion concentration of the slurry to 3000 ppm. Then, by following the same procedures as in Example 7, crude 2,6-NDCA crystals were obtained. The composition of the crystals thus obtained and the residue of the heavy metal catalyst in the crystals are shown in Table 2.

EXAMPLE 9

After adding 800 g acetic acid having a water content of 5% by weight to 1000 g oxidation product slurry obtained in Comparative Example 6, sodium bromide was further added so as to adjust the bromide ion concentration of the slurry to 4000 ppm. Then, by following the same procedures as in Example 7, crude 2,6-NDCA crystals were obtained. The composition of the crystals thus obtained and the residue of the heavy metal catalyst in the crystals are shown in Table 2.

EXAMPLE 10

To 1000 g oxidation product slurry obtained in Comparative Example 6, was added 1200 g acetic acid having a water content of 5% by weight Then, by following the same procedures as in Example 7, crude 2,6-NDCA crystals were obtained. The composition of the crystals thus obtained and the residue of the heavy metal catalyst in the crystals are shown in Table 2.

TABLE 2

|  | Com. Ex. 6 | Ex. 7 | Ex 8 | Ex. 9 | Ex. 10 |
| --- | --- | --- | --- | --- | --- |
| 2,6-NDCA concentration in oxidation product (wt. %) | 30.8 | 23.6 | 17.1 | 17.1 | 14.0 |

TABLE 2-continued

|  | Com. Ex. 6 | Ex. 7 | Ex 8 | Ex. 9 | Ex. 10 |
|---|---|---|---|---|---|
| Water in mother liquor (wt. %) | 10.4 | 9.1 | 7.7 | 7.5 | 7.1 |
| Bromide ion in mother liquor (wt. %) | 0.33 | 0.50 | 0.30 | 0.40 | 0.12 |
| Composition of crystals (wt. %) |  |  |  |  |  |
| 2,6-NDCA | 97.4 | 98.1 | 98.2 | 98.1 | 98.2 |
| TMA | 0.650 | 0.069 | 0.037 | 0.113 | 0.029 |
| 2-Formyl-6-naphthoic acid | 0.251 | 0.253 | 0.253 | 0.253 | 0.254 |
| Cobalt | 0.104 | 0.031 | 0.018 | 0.025 | 0.014 |
| Manganese | 0.088 | 0.011 | 0.006 | 0.017 | 0.004 |
| Cobalt residue (%) | 8.7 | 2.6 | 1.5 | 2.1 | 1.2 |
| Manganese residue (%) | 29.6 | 3.6 | 1.8 | 5.6 | 1.5 |

EXAMPLE 11

To 1000 g oxidation product slurry obtained in Comparative Example 6, was added 1200 g acetic acid having a water content of 5% by weight. The resultant slurry was kept at about 70° C. for 15 minutes under stirring, and then, the slurry was subjected to solid-liquid separation by suction filtration using a glass filter. The cake thus separated was dispersed in an amount of acetic acid having a water content of 5% by weight to obtain 1600 g slurry. After keeping at about 70° C. for 15 minutes under stirring, the slurry was subjected again to solid-liquid separation by suction filtration using a glass filter. The composition of the crystals obtained by drying the resulting cake and the residue of the heavy metal catalyst in the crystals are shown in Table 3.

COMPARATIVE EXAMPLE 7

The oxidation reaction was conducted in the same manner as in Comparative Example 6 except for changing the cobalt content to 0.20% by weight and the manganese content to 0.60% by weight to obtain 10.3 kg oxidation product slurry. The concentration of 2,6-NDCA in the slurry was 30.2% by weight ((Co+Mn)/DMN=0.060 and Mn/Co=3.22).

The yield based on 2,6-dimethylnaphthalene supplied was 93.9 mol % for 2,6-NDCA, 2.5 mol % for TMA and 0.31 mol % for 2-formyl-6-naphthoic acid.

After adding to 1000 g slurry thus obtained 1200 g acetic acid having a water content of 5% by weight, the resulting slurry was subjected to solid-liquid separation in the same manner as in Example 11. After the cake thus separated was dispersed in an amount of acetic acid having a water content of 5% by weight, the resultant slurry was subjected again to solid-liquid separation in the same manner as in Example 11. The cake thus obtained was dried to obtain crude 2,6-NDCA crystals. The composition of the crystals and the residue of the heavy metal catalyst in the crystals are shown in Table 3.

Since the ratio of manganese to cobalt in the catalyst was higher, a large amount of the heavy metal catalyst remained in the 2,6-NDCA crystals even after the washing as is the case of Comparative Example 3.

TABLE 3

|  | Ex. 11 | Com. Ex. 7 |
|---|---|---|
| Composition of dried crystals (wt. %) |  |  |
| 2,6-NDCA | 98.2 | 96.4 |
| TMA | 0.044 | 1.397 |
| 2-Formyl-6-naphthoic acid | 0.254 | 0.284 |
| Cobalt | 0.0271 | 0.0261 |
| Manganese | 0.0071 | 0.312 |
| Cobalt residue (%) | 2.3 | 6.6 |
| Manganese residue (%) | 2.4 | 26.2 |

EXAMPLE 12

The mother liquor and the washings in Example 10 was combined to obtain a combined liquid having a cobalt content of 0.150% by weight, a manganese content of 0.037% by weight and a water content of 5.3% by weight. After adding 0.9 g oxalic acid dihydrate to 200 g combined liquid, the resulting liquid was stirred for 10 minutes. The precipitates thus formed was filtered off to obtain a mother liquor having a cobalt content of 1.2 ppm and a manganese content of 15 ppm. Cobalt and manganese were recovered from the oxalic acid salts in a recovery rate of 99.92% by weight for cobalt and 96.0% by weight for manganese.

From the sum of the residual amount of the catalyst metal in the 2,6-NDCA crystals obtained in Example 10 and the amount of the catalyst metal not recovered from the mother liquor in this example, the overall recovery rate of the oxidation catalyst throughout the process was calculated as 98.7% by weight for cobalt and 94.6% by weight for manganese, showing extremely high recovery rates.

EXAMPLE 13

To the combined liquid of the mother liquor and the washings of Example 10, was added an amount of 47% by weight hydrobromic acid to prepare a sample liquid having a cobalt content of 0.149% by weight, a manganese content of 0.037% by weight, a bromide ion content of 0.56% by weight and a water content of 5.8% by weight. The molar ratio of bromide ion to metals was 2.2.

The sample liquid was passed through a jacketed ion exchange column (inner diameter of 20 mm and kept at 70° C.) at a flow rate of 250 g/hr over 2.5 hours. The ion exchange column was packed with 50 ml weakly basic anion exchange resin (IRA95SB, product of Organo Co., Ltd.) which was pretreated by passing a hydrobromic acid solution in acetic acid to change to bromide ion type. The composition of the effluent and the recoveries of metals and bromine are shown in Table 4.

Then, acetic acid having a water content of 35% by weight was passed through the exchange column at a flow rate of 250 g/hr for 1 hour to elute the adsorbed catalyst. The amounts of the metals and bromide ion in the eluate corresponded to the respective adsorbed amounts.

From the sum of the residual amount of the catalyst metals in the 2,6-NDCA crystals obtained in Example 10 and the amount of the catalyst metal not recovered from the mother liquor in this example, the overall recovery rate of the oxidation catalyst throughout the process was calculated as 98.6% by weight for cobalt and 93.7% by weight for manganese, showing extremely high recovery rates.

REFERENCE EXAMPLE 1

The same ion exchange process for recovering the catalyst as in Example 13 was repeated except for adding an amount of 47% by weight hydrobromic acid and water to the combined liquid of the mother liquor and the washings of Example 10 to prepare a sample liquid having a cobalt content of 0.130% by weight, a manganese content of 0.032% by weight, a bromide ion content of 0.49% by weight and a water content of 18% by weight. The molar ratio of bromide ion to metals was 2.2. The composition of the effluent and the recoveries of metals and bromine are shown in Table 4.

Since the water content was high, the recovery rate of the catalyst was poor.

TABLE 4

|  | Ex. 13 | Ref. Ex. 1 |
| --- | --- | --- |
| Composition of sample liquid (wt. %) | | |
| Cobalt | 0.149 | 0.130 |
| Manganese | 0.037 | 0.032 |
| Bromine | 0.56 | 0.49 |
| Water | 5.8 | 18.0 |
| Composition of effluent (wt. %) | | |
| Cobalt | 0.00033 | 0.0137 |
| Manganese | 0.0018 | 0.0186 |
| Bromine | 0.060 | 0.139 |
| Catalyst recovery (%) | | |
| Cobalt | 99.78 | 89.4 |
| Manganese | 95.1 | 42.4 |
| Bromine | 89.3 | 71.7 |

EXAMPLE 14

Cobalt acetate tetrahydrate, manganese acetate tetrahydrate, 47% by weight hydrobromic acid and water were dissolved into 7 kg glacial acetic acid to prepare a catalyst solution having a cobalt content of 0.36% by weight, a manganese content of 0.08% by weight, a bromine content of 0.40% by weight and a water content of 2% by weight.

Into a 3-liter titanium reactor equipped with a stirrer and a reflux condenser, were charged 1200 g of the catalyst solution. Separately, 2,6-dimethylnaphthalene with a purity of 99.7% by weight was melted in a tank by heating to 120° C. or higher.

The inner pressure of the reactor was adjusted to 14 kgf/cm$^2$ G by introducing nitrogen gas and the contents was heated to 200° C. under stirring. After the temperature and pressure reached steady states, the oxidation reaction was permitted to proceed while simultaneously supplying the molten 2,6-dimethylnaphthalene at a flow rate of 100 g/hr and compressed air at a flow rate about 0.2 Nm$^3$/hr to the reactor. After 150 g 2,6-dimethylnaphthalene were supplied to the reactor (90 minutes after the initiation of oxidation reaction), the supply of the catalyst solution to the reactor was started at a flow rate of 800 g/hr while removing the oxidation product from the reactor to a receiving tank maintained at ordinary pressure so that the upper surface of the liquid in the reactor kept its level constant.

After the reaction was continued for about 8 hours, the supply of 2,6-dimethylnaphthalene, the catalyst solution and air was stopped to cease the reaction, thereby obtaining 8.2 kg slurry of the oxidation product including the slurry remaining in the reactor. The concentration of 2,6-NDCA in the slurry was 14.6% by weight.
(0016)
Into a beaker, were placed 140 g oxidation product slurry obtained above, to which 7.15 g of 0.1% by weight aqueous solution of an anionic polymer flocculant (Kurifarm PA404 available from Kurita Water Industries, Ltd.) was added at room temperature (24° C.) under stirring at 160 rpm. The amount of the flocculant added was 0.035% by weight based on the amount of the 2,6-naphthalenedicarboxylic acid crystals. The stirring was further continued for 10 minutes at 160 rpm and for 15 minutes at 80 rpm to complete the flocculating treatment. The average particle size of the flocculates formed in the slurry was determined by a laser diffraction particle size analyzer. The slurry after the flocculating treatment was suction-filtered under a pressure of 50 mmHg lower than atmospheric pressure through 5B filter paper (70 mm diameter) placed on Buchner funnel. The time required for the filtrate to reach 70 ml from 20 ml (filtering time) was measured. The results are shown in Table 5.

EXAMPLES 15 to 16

The same flocculating treatment as in Example 14 was repeated except for using a nonionic polymer flocculant (Accofloc N100 available from Mitsui Cytec, Ltd.) or a cationic polymer flocculant (Sanfloc CE-683P available from Sanyo Chemical Industries, Ltd.). The average particle size of the flocculates and the filtering time are shown in Table 5.

EXAMPLE 17

The same flocculating treatment as in Example 14 was repeated except that 15.3 g of 0.4% by weight aqueous solution of the anionic polymer flocculant was added to change the amount of the flocculant to 0.30% by weight based the amount of 2,6-naphthalenedicarboxylic acid. The average particle size of the flocculates and the filtering time are shown in Table 5.

EXAMPLE 18

The same flocculating treatment as in Example 14 was repeated except that 20.4 g of 0.4% by weight aqueous solution of the anionic polymer flocculant was added to change the amount of the flocculant to 0.40% by weight based the amount of 2,6-naphthalenedicarboxylic acid. The average particle size of the flocculates and the filtering time are shown in Table 5.

EXAMPLE 19

Into a three-necked flask, were placed 140 g oxidation product slurry obtained in Example 14, which was then heated to 100° C. under refluxing. To the resultant slurry, was added 7.15 g of 0.1% by weight aqueous solution of an anionic polymer flocculant (Kurifarm PA404 available from Kurita Water Industries, Ltd.) under stirring at 160 rpm. The amount of the flocculant was 0.035% by weight based on the amount of the 2,6-naphthalenedicarboxylic acid crystals. The stirring was further continued for 10 minutes at 160 rpm and for 15 minutes at 110 rpm to complete the flocculating treatment. The average particle size of the flocculates and the filtering time were measured in the same manner as in Example 14 except that the slurry kept at 100° C. was filtered without cooling. The results are shown in Table 5.

EXAMPLES 20 to 21

The same flocculating treatment at 100° C. as in Example 19 was repeated except for using a nonionic polymer flocculant (Accofloc N100 available from Mitsui Cytec, Ltd.) or a cationic polymer flocculant (Sanfloc CE-683P available from Sanyo Chemical Industries, Ltd.). The average particle size of the flocculates and the filtering time are shown in Table 5.

REFERENCE EXAMPLE 2

The same procedures as in Example 14 were repeated except for adding no flocculant. The average particle size of the flocculates and the filtering time are shown in Table 5.

REFERENCE EXAMPLE 3

Into a three-necked flask, were placed 140 g oxidation product slurry obtained in Example 14, which was then heated to 100° C. under refluxing. By following the same procedures as in Example 19 except for using no flocculant, the average particle size of the flocculates in the slurry and the filtering time were measured. The results are shown in Table 5.

TABLE 5

| | Flocculant | Addition amount (wt. %) | Flocculating temperature (° C.) | Average particle size of flocculates (μm) | Filtering time (sec) |
|---|---|---|---|---|---|
| Example 14 | Anionic | 0.035 | 24 | 89 | 104 |
| Example 15 | Nonionic | 0.035 | 24 | 80 | 149 |
| Example 16 | Cationic | 0.035 | 24 | 77 | 154 |
| Example 17 | Anionic | 0.30 | 24 | 113 | 87 |
| Example 18 | Anionic | 0.40 | 24 | 111 | 90 |
| Example 19 | Anionic | 0.035 | 100 | 82 | 17 |
| Example 20 | Nonionic | 0.035 | 100 | 77 | 22 |
| Example 21 | Cationic | 0.035 | 100 | 74 | 26 |
| Comparative Example 8 | — | — | 24 | 14 | 403 |
| Comparative Example 9 | — | — | 100 | 15 | 70 |

As seen from the examples, according to the present invention, (1) the naphthalenedicarboxylic acid is produced in a high yield while minimizing the by-production of trimellitic acid, etc.; (2) the purification of the crude naphthalenedicarboxylic acid is easy because of the minimized incorporation of the heavy metal catalyst into the naphthalenedicarboxylic acid crystals due to complexation of benzotricarboxylic acid such as trimellitic acid with the catalyst metals; (3) the expensive catalyst metals are easily recovered in an extremely high rate; (4) the energy consumed for recovering the solvent is small because the amount of water used in the process is small; and (5) the addition of the polymer flocculant increases the particle size of 2,6-naphthalenedicarboxylic acid crystals to facilitate the separation and recovery of the crystals, thereby making it possible to use the centrifugal filter and vacuum filter which are difficult to be applied to the conventional process. Additionally, the throughput of the centrifugal decanter is increased.

Thus, the process according to the present invention is quite advantageous for the industrial production of the naphthalenedicarboxylic acid.

What is claimed is:

1. A method of producing naphthalenedicarboxylic acid, which comprises the steps of:
    oxidizing dialkylnaphthalene to naphthalenedicarboxylic acid at 160 to 240° C. in a solvent containing a lower aliphatic carboxylic acid using a molecular oxygen-containing gas in the presence of a catalyst comprising a cobalt compound, a manganese compound and a bromine compound to obtain an oxidation product mixture, and
    subjecting said oxidation product mixture to a solid-liquid separation to obtain crystals of naphthalenedicarboxylic acid and a mother liquor when a concentration of naphthalenedicarboxylic acid in said oxidation product mixture is 8 to 30% by weight,
    an atomic ratio of manganese to cobalt of said catalyst being 0.03 to 0.5, and said catalyst being supplied to an oxidation reaction zone so that a total of cobalt and manganese is 0.025 to 0.1 gram atom based on 1 gram atom of said dialkylnaphthalene, and wherein a compound capable of forming bromide ions is added to said oxidation product mixture prior to said solid-liquid separation.

2. The method of producing naphthalenedicarboxylic acid according to claim 1, wherein a polymer flocculant is added to said oxidation reaction zone or said oxidation product mixture prior to said solid-liquid separation.

3. The method of producing naphthalenedicarboxylic acid according to claim 1, wherein said crystals of naphthalenedicarboxylic acid obtained by said solid-liquid separation of said oxidation product mixture are washed with a lower aliphatic carboxylic acid having a water content of 10% by weight or less.

4. A method of producing naphthallenedicarboxylic acid, which comprises the steps of:
    oxidizing dialkylnaphthalene to napthalenedicarboxylic acid at 160 to 240° C. in a solvent containing a lower aliphatic carboxylic acid using a molecular oxygen-containing gas in the presence of a catalyst comprising a cobalt compound, a manganese compound and a bromine compound to obtain an oxidation product mixture, and
    subjecting said oxidation product mixture to a solid-liquid separation to obtain crystals of napthalenedicarboxylic acidand a mother liquid when a concentration of napthalenedicarboxylic acid in said oxidation product mixture is 8 to 30% by weight,
    an atomic ratio of manganese to cobalt of said catalyst being 0.03 to 0.5, and said catalyst being supplied to an oxidation reaction zone so that a total of cobalt and manganese is 0.025 to 0.1 gram atom based on 1 gram atom of said dialkylnapthlene, and wherein a polymer floccuant is added to said oxidation reaction zone or said oxidation product mixture prior to said solid-liquid separation.

5. The method of producing naphthalenedicarboxylic acid according to claim 4, wherein said crystals of naphthalenedicarboxylic acid obtained by said solid-liquid separation of said oxidation product mixture are washed with a lower aliphatic carboxylic acid having a water content of 10% by weight or less.

6. The method of producing naphthalenedicarboxylic acid according to claim 2, wherein said crystals of naphthalenedicarboxylic acid obtained by said solid-liquid separation of said oxidation product mixture are washed with a lower aliphatic carboxylic acid having a water content of 10% by weight or less.

7. The method of producing naphthalenedicarboxylic acid according to claim 1, wherein said crystals of naphthalenedicarboxylic acid obtained by said solid-liquid separation of said oxidation product mixture are re-dispersed in a lower aliphatic carboxylic acid having a water content of 10% by weight or less to obtain a dispersion which is then subjected to a solid-liquid separation into crystals of naphthalenedicarboxylic acid and a mother liquor.

8. The method of producing naphthalenedicarboxylic acid according to claim 4, wherein said crystals of naphthalenedicarboxylic acid obtained by said solid-liquid separation of said oxidation product mixture are re-dispersed in a lower aliphatic carboxylic acid having a water content of 10% by weight or less to obtain a dispersion which is then subjected to a solid-liquid separation into crystals of naphthalenedicarboxylic acid and a mother liquor.

9. The method of producing naphthalenedicarboxylic acid according to claim 2, wherein said crystals of naphthalenedicarboxylic acid obtained by said solid-liquid separation of said oxidation product mixture are re-dispersed in a lower aliphatic carboxylic acid having a water content of 10% by weight or less to obtain a dispersion which is then subjected to a solid-liquid separation into crystals of naphthalenedicarboxylic acid and a mother liquor.

10. The method of producing naphthalenedicarboxylic acid according to claim 7, wherein at least a portion of said mother liquor from said solid-liquid separation after re-dispersion is recycled to a next oxidation product mixture which is then subjected to a solid-liquid separation.

11. The method of producing naphthalenedicarboxylic acid according to claim 8, wherein at least a portion of said mother liquor from said solid-liquid separation after re-dispersion is recycled to a next oxidation product mixture which is then subjected to a solid-liquid separation.

12. The method of producing naphthalenedicarboxylic acid according to claim 9, wherein at least a portion of said mother liquor from said solid-liquid separation after re-dispersion is recycled to a next oxidation product mixture which is then subjected to a solid-liquid separation.

13. The method of producing naphthalenedicarboxylic acid according to claim 1, wherein said dialkylnaphthalene is 2,6-dimethylnaphthalene.

14. The method of producing naphthalenedicarboxylic acid according to claim 1, wherein the compound capable of forming bromine ions is selected from the group consisting of hydrobromic acid, sodium bromide and potassium bromide.

15. The method of producing naphthalenedicarboxylic acid according to claim 14, wherein the compound capable of forming bromine ions is hydrobromic acid.

16. The method of producing naphthalenedicarboxylic acid according to claim 1, wherein the compound capable of forming bromine ions is added in an amount of 2000–6000 ppm.

17. The method of producing naphthalenedicarboxylic acid according to claim 1, wherein the compound capable of forming bromine ions is added in an amount of 3000–5000 ppm.

18. The method of producing naphthalenedicarboxylic acid according to claim 1, wherein said dialkylnaphthalene is 2,6-dimethylnaphthalene.

19. The method of producing naphthalenedicarboxylic acid according to claim 4, wherein the polymer flocculant is added to said oxidation product mixture prior to said solid-liquid separation.

20. The method of producing naphthalenedicarboxylic acid according to claim 4, wherein said polymer flocculant is a water-soluble polymer.

21. The method of producing naphthalenedicarboxylic acid according to claim 4, wherein said polymer flocculant is selected from the group consisting of anionic, nonionic, cationic and amphoteric polymer flocculants.

22. The method of producing naphthalenedicarboxylic acid according to claim 4, wherein said polymer flocculant is at least one selected from the group consisting of sodium polyacrylate, acrylic amide-sodium acrylate copolymer, polyacrylic amide, starch, gelatin, Mannich-modified polyacrylic amide, polyalkylaminoacrylate, polyalkylaminomethacrylate, chitosan and acrylic amide-aminoalkylacrylate quaternary salt-acrylic acid copolymer.

23. The method of producing naphthalenedicarboxylic acid according to claim 4, wherein the polymer flocculant is added in an amount of 0.005 to 0.4% by weight based on the amount of naphthalenedicarboxylic acid crystals.

* * * * *